United States Patent [19]

Englert et al.

[11] Patent Number: 5,360,808
[45] Date of Patent: Nov. 1, 1994

[54] ARYLCARBONYLAMINOALKYL-DIHYDRO-OXO-PYRIDINES, THEIR PRODUCTION AND THEIR USE

[75] Inventors: Heinrich Englert, Hofheim am Taunus; Dieter Mania, Königstein/Taunus, both of Germany; David Wettlaufer, Phillipsburg, N.J.; Erik Klaus, Kelkheim, Germany

[73] Assignee: Hoechst Aktiengesellschaft, Frankfurt am Main, Germany

[21] Appl. No.: 19,296

[22] Filed: Feb. 18, 1993

[30] Foreign Application Priority Data

Feb. 20, 1992 [EP] European Pat. Off. ........ 92102828.8

[51] Int. Cl.$^5$ .................. C07D 213/64; A61K 31/44
[52] U.S. Cl. .................. 514/335; 546/261; 546/291; 546/298; 544/360
[58] Field of Search .................. 546/261; 514/335

[56] References Cited

U.S. PATENT DOCUMENTS 4,312,875  1/1982  Lesher et al. .................. 514/334

FOREIGN PATENT DOCUMENTS

| 2038683 | 7/1984 | Australia | 544/238 |
|---|---|---|---|
| 0347027 | 12/1989 | European Pat. Off. | 546/288 |
| 2470124 | 5/1981 | France | 546/298 |
| 2637477 | 2/1978 | Germany | 546/298 |
| 77/5045 | 8/1977 | South Africa | 546/298 |
| 8400756 | 3/1984 | WIPO | 546/257 |

OTHER PUBLICATIONS

V. H. Wissman et al., Angew. Chemie 1980, 92(2), 129–130.

J. Org. Chem. 1980, 45, "Photochemical Syntheses of 1,2-Diazepines. 11.1 Regiospecific Synthesis of 1,2-Dihydro-1,2-diazepin-3-ones", pp. 5095–5100.

Primary Examiner—Alan L. Rotman
Attorney, Agent, or Firm—Finnegan, Henderson, Farabow, Garrett & Dunner

[57] ABSTRACT

Arylcarbonylaminoalkyl-dihydro-oxo-pyridines of Formula I

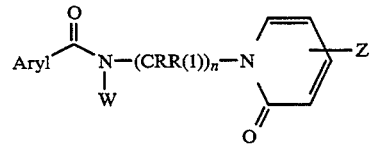

are disclosed wherein aryl is an aromatic or heteroaromatic system, n is zero through 5; R and R(1), are hydrogen, or loweralkyl; W is hydrogen, (hetero)-(aryl)-loweralkyl; Z is hydrogen, $CH_2OR(2)$, CHO, (CO)OR(2), $(CO)NR(2)_2$.

Processes for the preparation of compound I are also disclosed.

Compounds I are suitable for the treatment of disorders of the cardiovascular system, for example of hypertension, of cardiac insufficiency or of disturbances of blood flow in the coronary systems such as, for example, angina. Disturbances of cerebral and peripheral blood flow are likewise influenced beneficially. Furthermore, compounds I are able to influence smooth-muscle organs such as uterus, bronchi, intestines and biliary system, the urinary tract (ureter, bladder and urethra) in the sense of spasmolysis. They are therefore also suitable for the treatment of diseases associated with spasms of these organs, for example for the treatment of premature labor in pregnancy, of ureteral or biliary colic, of obstructive airway diseases such as asthma, of disturbances of intestinal motility such as, for example, of irritable colon or of bladder incontinence. Additionally, compounds of formula 1 can serve as anticonvulsants in the treatment of epilepsy.

4 Claims, No Drawings

ARYLCARBONYLAMINOALKYL-DIHYDRO-OXO-PYRIDINES, THEIR PRODUCTION AND THEIR USE

The present invention relates to arylcarbonylaminoalkyl-dihydro-oxo-pyridines of Formula I

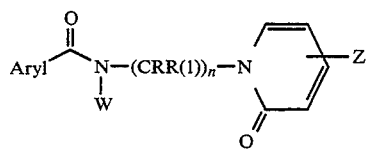

wherein aryl is an aromatic or heteroaromatic system unsubstituted or substituted with 1 to 3 identical or different halogen, loweralkyl, loweralkoxy, or trifluoromethyl radicals; n is zero through 5; R and R(1), independently for each carbon (n is zero through 5), are independently hydrogen, or loweralkyl; W is hydrogen, loweralkyl, arylloweralkyl, or heteroarylloweralkyl; Z is hydrogen, $CH_2OR(2)$, CHO, (CO)OR(2), $(CO)NR(2)_2$; R(2) is independently hydrogen, loweralkyl, cycloalkyl, bicycloalkyl, aryl, arylloweralkyl, heteroaryl, or heteroarylloweralkyl.

As used throughout the specification and claims, the term "alkyl" refers to a straight or branched chain hydrocarbon radical containing no unsaturation and having 1 to 8 carbon atoms such as methyl, ethyl, 1-propyl, 2-propyl, 1-butyl, 1-pentyl, 1-hexyl, and the like; the term "cycloalkyl" refers to a cycloalkyl hydrocarbon radical containing no unsaturation. This cycloalkyl hydrocarbon radical can also have additional substituents such as one or more alkyl, alkoxy, hydroxy, or trifluoromethyl groups. Examples include, but are not limited to cyclobutyl, cyclopentyl, cyclohexyl, cycloheptyl, cyclooctyl, 4-methylcyclohexyl, and the like; the term "bicycloalkyl" refers to a bicycloalkyl hydrocarbon radical containing no unsaturation. This bicycloalkyl hydrocarbon radical can also have additional substituents such as one or more alkyl, alkoxy, hydroxy, or trifluoromethyl groups. Examples include, but are not limited to, exo-2-norbornyl, endo-2-norbornyl, myrtanyl, and the like; the term "aryl" refers to a phenyl group or a phenyl group substituted by one or more alkyl, halogen, alkoxy or trifluoromethyl groups; the term "heteroaryl" refers to an aromatic heterocycle or an aromatic heterocycle substituted by one or more alkyl, halogen, alkoxy, or trifluoromethyl groups. Examples include, but are not limited to, 2-pyridinyl, 3-pyridinyl, 4-pyridinyl, 2-thienyl, 2-furfuryl, 1-methyl-2-pyrrolo, pyrazinyl, quinolyl, and the like; the term "alkoxy" refers to a monovalent substituent which consists of an alkyl group linked through an ether oxygen and having its free valence bond from the ether oxygen. Examples of alkoxy groups are methoxy, ethoxy, 1-propoxy, 2-propoxy, 1-butoxy, 1-pentoxy, 2-pentoxy, 3-hexoxy, 4-heptoxy, 2-octoxy, and the like; the term "alkanol" refers to a compound formed by a combination of an alkyl group and a hydroxy radical. Examples of alkanols are methanol, ethanol, 1- and 2-propanol, and the like; the term "halogen" refers to a member of the family consisting of fluorine, chlorine, bromine, and iodine. The term "lower" as applied to any of the aforementioned groups refers to a group having a carbon skeleton containing up to and including 8 carbon atoms.

The compounds of the present invention which lack an element of symmetry exist as optical antipodes and as the racemic forms thereof. The optical antipode may be prepared from optically pure intermediates derived from racemic mixtures by standard optical resolution techniques, such as, for example, separation by chromotography using chiral phases, the separation of diastereomeric salts of instant compounds characterized by the presence of a basic amino group and an optically active acid, or by separation (via crystallization or chromotography) of diastereomeric derivatives from which an optically pure intermediate can be derived.

Preferred compounds of formula I are these in which aryl is an unsubstituted or substituted aromatic or heteroaromatic system with Z representing hydrogen, (CO)OR(2), and $(CO)NR(2)_2$, and n, R, R(1), and R(2) being defined as above.

Additionally preferred are compounds of the formula I in which aryl represents and unsubstituted or substituted phenyl, pyridinyl, quinolinyl, and pyrazinyl with Z representing hydrogen, (CO)OR, and $(CO)NR(2)_2$, and n, R, R(1), and R(2) being defined as above.

Very particularly preferred compounds of formula I are those in which aryl is an unsubstituted or substituted pyridinyl with Z representing hydrogen, (CO)OR(2) and $(CO)NR(2)_2$, and n, R, R(1), and R(2) being defined as above.

Especially preferred are compounds selected from the group consisting of 1,6-dihydro-1-[2-(2-pyridinylcarbonylamino)ethyl]-6-oxo-3-pyridinecarboxylic acid methyl ester, 1,6-dihydro-6-oxo-1-[2-(2-pyrazinylcarbonylamino)ethyl]-3-pyridinecarboxylic acid methyl ester, 1,6-dihydro-6-oxo-1-[2-(3quinolinylcarbonylamino)ethyl]-3-pyridinecarboxylicacid methyl ester, 1-[2-benzoylaminoethyl)-1,6-dihydro-6-oxo-3-pyridinecarboxylic acid methyl ester.

Animal experimental investigations show that they are suitable for the treatment of disorders of the cardiovascular system, for example for the treatment of hypertension, of cardiac insufficiency or of disturbances of blood flow in the coronary systems such as, for example, angina. Disturbances of cerebral and peripheral blood flow are likewise influenced beneficially. Furthermore, compounds I are able to influence smooth-muscle organs such as uterus, bronchi, intestines and biliary system, the urinary tract (ureter, bladder and urethra) in the sense of spasmolysis. They are therefore also suitable for the treatment of diseases associated with spasms of these organs, for example for the treatment of premature labor in pregnancy, of ureteral or biliary colic, of obstructive airway diseases such as asthma, of disturbances of intestinal motility such as, for example, of irritable colon or of bladder incontinence. Additionally, compounds of formula I can serve as anti-convulsants in the treatment of epilepsy and as hair growth inducers in the treatment of baldness.

The invention additionally relates to the processes for the preparation of the compound I outlined in Reaction Schemes A, B, C, and D.

To gain entry into compounds of Formula I, which contain a 1,6-dihydro-6-oxo-3-pyridinecarboxylic acid radical, two synthetic routes are used.

The appropriate arylcarboxylic acid ester II is condensed with excess diamine III, wherein aryl, n is 0 and 2 through 5, R, R(1), and loweralkyl are as herein before described, to provide aminocarboxamide IV (Reaction Scheme A). The condensation can be conducted in an alkanol solvent such as, for example, methanol, ethanol, 1-propanol, of 2-propanol. Ethanol or methanol are preferred. The condensation temperature is not critical; it is desirable, however, to perform the reactions at a temperature of between 0° C. and reflux, a temperature range of about 20° to 25° C. being preferred. Condensation of IV with 2-oxo-2Hopyran-5-carboxylic acid methyl ester (coumalic acid methyl ester) (V) results in construction of the dihydro-oxo-pyridine radical, where Z is 3-$CO_2CH_3$, in I. The condensation can be conducted in an alkanol solvent such as, for example, methanol, ethanol, 1-propanol, or 2-propanol. Ethanol is preferred. The condensation temperature is not critical; it is desirable, however, to perform the reactions at a temperature of between 0° C. and reflux, a temperature range of 20°-45 ° C. being preferred.

These same compounds are available via a similar approach in which diamine III, n is 0 and 2 through 5, is condensed with 2-oxo-2H-pyran-5-carboxylic acid methyl ester (V) (Reaction Scheme B) in an alkanol solvent such as, for example, methanol, ethanol, 1-propanol, or 2-propanol. Ethanol is preferred. The condensation temperature is not critical; it is desirable, however, to perform the reactions at a temperature of between 0° C. and reflux, a temperature range of about 20° to 25° C. being preferred. The resulting amine VI (Z is 3-$CO_2CH_3$) is further condensed with an arylcarboxylic acid chloride VII to give I (Z is 3-$CO_2CH_3$). This condensation is conducted in a non-protic solvent such as dimethylformamide, dimethylacetamide, acetonitrile, dichloromethane, chloroform, or dimethylsulfoxide, in the presence of an alkali metal carbonate such as potassium carbonate or potassium hydrogen carbonate, and the like, or an organic base such as, for example, triethylamine, collidine, pyridine, and the like at a temperature of −25° to 40° C. Pyridine in dimethylformamide at 0° C. are the preferred reaction conditions.

Alternatively, amine VI (Z is 3-$CO_2CH_3$) can also be condensed with an arylcarboxylic acid (VIII) (Reaction Scheme B) in a non-protic solvent such as dimethylformamide, dimethylacetamide, acetonitrile, chloroform, dichloromethane, or dimethylsulfoxide in the presence of a coupling agent such as 1,3-dicyclohexylcarbodiimide, 1,3-diisopropylcarbodiimide, or 2,4,6-tripropyl-2,4,6-trioxo-1,3,5,2,4,6-trioxatriphosphorinane (propylphosphonic acid anhydride, V. H. Wissman, et al, Angew. Chemie 1980, 92(2), 129) at a temperature of −10 to 80° C. Dichloromethane and/or dimethylformamide with propylphosphonic acid anhydride at −8 to 25° C. are the preferred reaction conditions.

The arylcarbonylaminoalkyl-dihydro-oxo-pyridines of Formula I are accessible via the condensation of N-(haloalkyl)phthalimide IX with hydroxypyridine X, wherein n is 1 through 5 with Z and halogen are as herein before described (Reaction Scheme C). The condensation can be conducted in a dipolar aprotic solvent such as acetonitrile, dimethylacetamide, dimethylformamide, of dimethylsulfoxide at a temperature of 0°to 100° C. The preferred solvent is dimethylformamide at a temperature of 50° C. Removal of the phthalimide group from XI, is carried out by treatment with aqueous methylamine or anhydrous hydrazine in an alkanol solvent such as, for example, methanol, ethanol, 1-propanol, or 2-propanol at a temperature of 0° C. to reflux. The preferred reagent is anhydrous hydrazine in ethanol at reflux. The resulting amine VI is further condensed with an arylcarboxylic acid chloride to give I. This condensation is conducted in a nonprotic solvent such as dimethylformamide, dimethylacetamide, acetonitrile, dichloromethane, or dimethylsulfoxide, in the presence of an alkyl metal carbonate such as potassium carbonate and the like, or an organic base such as, for example, triethylamine, collidine, pyridine, and the like at a temperature of −25° to 40° C. Pyridine in dichloromethane at 0° C. to room temperature are the preferred reaction conditions.

Reaction Scheme A

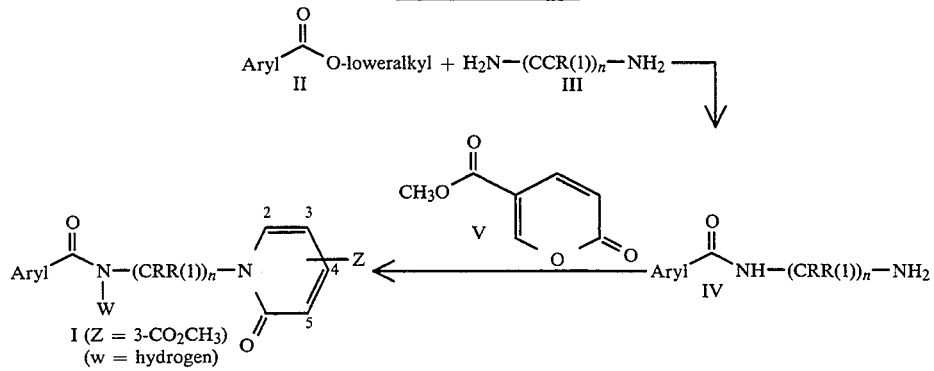

Reaction Scheme B

III + V ⟶

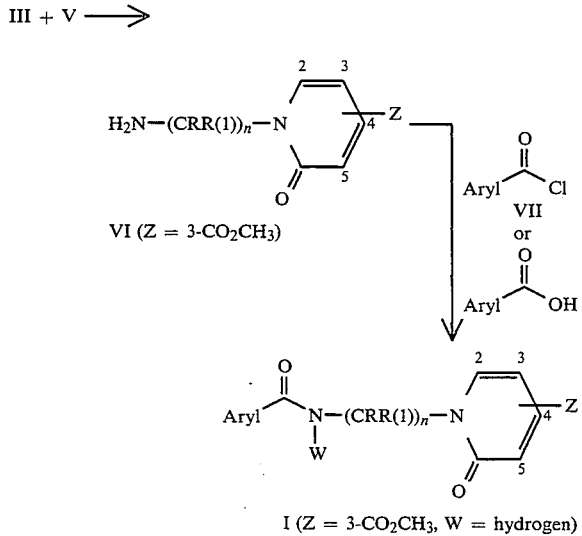

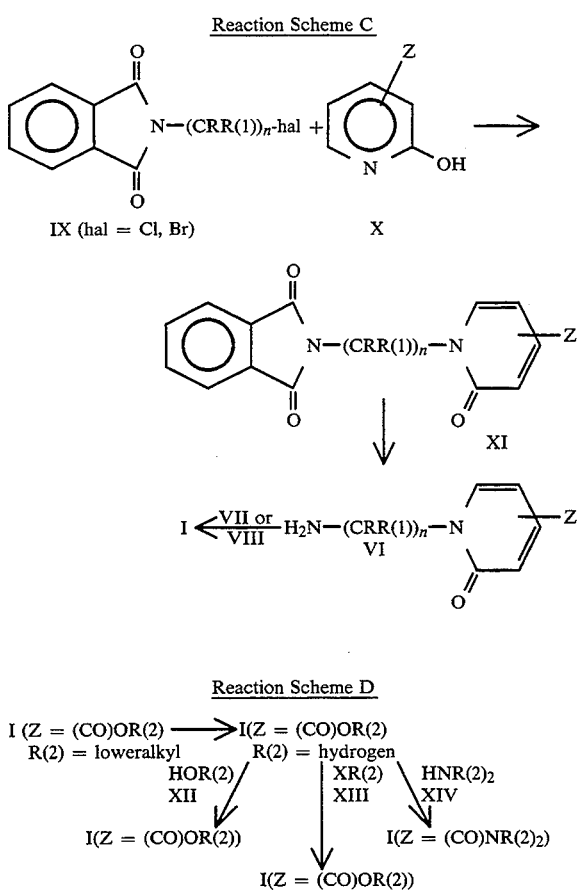

Reaction Scheme C

IX (hal = Cl, Br)   X

XI

I ⟵$\frac{\text{VII or}}{\text{VIII}}$ H$_2$N—(CRR(1))$_n$—N  VI

Reaction Scheme D

I (Z = (CO)OR(2)) ⟶ I(Z = (CO)OR(2))
R(2) = loweralkyl      R(2) = hydrogen
         HOR(2)/ XII       |XR(2) XIII   \HNR(2)$_2$ XIV
         I(Z = (CO)OR(2))  |              I(Z = (CO)NR(2)$_2$)
                    I(Z = (CO)OR(2))

The arylcarbonylalkyl-dihydro-oxo-pyridines of Formula I where Z is (COLOR(2)) and R(2) is hydrogen, are accessible through hydrolysis of the ester moiety where Z is (CO)OR(2) and R(2) is loweralkyl (Reaction Scheme D). The hydrolysis can be carried out in a mixture of water and a lower alkanol such as, for example, methanol, ethanol, 1-propanol, and 2-propanol in the presence of an alkali metal carbonate such as sodium carbonate, sodium bicarbonate, potassium carbonate and potassium hydrogen carbonate at a temperature of 0° C. to reflux. The preferred reaction conditions are water with methanol and sodium carbonate at 60° C.

Ester compounds of Formula I where Z is (CO)OR(2) and R(2) is as herein before described, except for hydrogen, can be prepared from the carboxylic acid of I (where Z is (CO)OR(2) and R(2)is hydrogen)(Reaction Scheme D). This can be carried out by conversion to the acid chloride (Formula I, Z is (CO)Cl) using standard reagents such as thionyl chloride and oxalyl chloride without solvent or a solvent such as benzene, dichloromethane, chloroform, 1,2-dichloroethane, ant the like at 0° C. to reflux. Thionyl chloride without additional solvent at reflux are the preferred reaction conditions. The acid chloride is converted to the desired ester by reaction with an alcohol, HOR(2) (XII, where R(2) is as herein before described, except for hydrogen), without solvent (neat) or in an aprotic solvent such as dimethylformamide, dimethylacetamide, dichloromethane, chloroform and the like. The coupling is done in the presence of a base. This can be done with an alkali metal carbonate such as, for example, potassium carbonate or potassium hydrogen carbonate, and the like, or an organic base such as, for example, triethyl amine, collidine, pyridine, and the like at a temperature of 0° C. to reflux. Pyridine with the alcohol without solvent at zero to 25° C. are the preferred reaction conditions.

Alternatively, carboxylic acid I (where Z is (CO)OR(2) and R(2) is hydrogen) can be alkylated with X-R(2) (XIII, Reaction Scheme D), wherein X is halogen, preferably bromine or iodine, and R(2) is as herein before described, except for hydrogen.

The reaction is carried out in a dipolar aprotic solvent such as dimethylformamide, dimethylacetamide, acetonitrile, dimethylsulfoxide, and the like in the presence of an alkali metal carbonate such as potassium carbonate, potassium hydrogen carbonate, sodium carbonate, and the like at a temperature of 0°to 120° C. Preferred conditions are dimethylformamide with potassium hydrogen carbonate at 50° C.

Compounds of Formula I where Z is (CO)NR(2)$_2$, where R" is as before herein described, are prepared from condensation of I, (where Z is (CO)OR(2) and R(2) is hydrogen), with HNR(2)$_2$ (XIV) in the presence of a coupling agent such as, for example, 1,3-dicyclohexylcarbodiimide, 1,3odiisopropylcarbodiimide, an¢2,4,6-tripropyl-2,4, 6-trioxo- 1,3,5,2,4,6-trioxatriphosphorinane (propylphosphonic acid anhydride, V. H. Wissman et al., Angew. Chemie 1980, 92(2), 129), and the like (Reaction Scheme D). The coupling temperature is not critical; however, it is desirable to perform the reaction at a temperature of between −10° to 80° C. in a non-protic solvent such as dichloromethane, chloroform, dimethylformamide, dimethylacetamide, dimethylsulfoxide, and the like. Dimethylformamide with propylphosphonic acid anhydride at −8° to 25° C. are the preferred conditions.

Compounds of formula I where W is loweralkyl, arylloweralkyl, or heteroarylloweralkyl are prepared by deprotonation of I (W is hydrogen with sodium hydride, potassium hydride, and the like in a polar aprotic solvent such as dimethylformamide, dimethylacetamide, dimethylsulfoxide, and the like at a temperature of zero to 40° C. Alkylation of the anion with an alkylating agent such as, for example, methyl iodide, dimethyl sulfate, 2-phenylethyl bromide, benzyl bromide, iodoethane, and the like at zero to 40° C. follows. Preferred reaction conditions are deprotonation in dimethylformamide with sodium hydride at 25° C. with alkylation at 25° C.

As already mentioned, the compounds I according to the invention can be used as antihypertensives, as coronary therapeutics, as agents for the treatment of cardiac insufficiency, or disturbances of cerebral and peripheral blood flow or of disturbances of intestinal tactility, premature labor, obstructions of the airways or of the urinary tract or of the biliary tract or as spasmolytics, and as agents for the treatment or epilepsy and baldness. The compounds can also be used for the treatment of cardiac rhythm disturbances and for the treatment of myocardial infarction.

In this connection, pharmaceuticals which contain the compound I can be administered orally, parenterally, intravenously, rectally or by inhalation, with the preferred form of adiministration being dependent on the disease which is to be treated. The compounds I can, moreover, be used alone or together with pharmaceutical auxiliaries, specifically both in veterinary and in human medicine.

The particular auxiliaries suitable for the desired pharmaceutical formulation are familiar to those skilled in the art on the basis of their expert knowledge. Besides solvents, gel-formers, suppository bases, tablet auxiliaries and other active substance vehicles, it is possible to use, for example, antioxidants, dispersing agents, emulsifiers, antifoam agents, flavorings, preservatives, stabilizers or colorants.

For a form for oral use, the active compounds are mixed with the additives suitable for this purpose, such as excipients, stabilizers or inert diluents, and converted by customary methods into suitable dosage forms such as tablets, coated tablets, hard gelatin capsules, aqueous, alcoholic or oily suspensions, or aqueous, alcoholic or oily solutions. Examples of inert vehicles which can be used are gum arabic, magnesia, magnesium carbonate, potassium phosphate, lactose, glucose or starch, especially corn starch. This preparation can be carried out both as dry and as wet granules. Examples of suitable oily excipients or solvents are vegetable; or animal oils, such as sunflower oil or fish liver oil.

For subcutaneous or intravenous administration, the active compounds are converted into solution, suspension or emulsion, if desired with the substances customary for these purposes, such as solubilizers, emulsifiers or other auxiliaries. Examples of suitable solvents are water, physiological saline solution or alcohols, for example, ethanol, propanol, glycerol, as well as sugar solutions such as glucose or mannitol solutions or else a mixture of the various solvents mentioned.

Examples of pharmaceutical formulations suitable for administration in the form of aerosols or sprays are solutions, suspensions or emulsions of the active substance of the formula I in a pharmaceutically acceptable solvent such as, in particular, ethanol or water, or a mixture of such solvents. The formulation can, if required, also contain other pharmaceutical auxiliaries such as surfactants, emulsifiers and stabilizers as well as a propellant gas. A preparation of this type usually contains the active substance in a concentration of about 0.1 to 10, in particular of about 0.3 to 3% by weight.

The dosage of the active substance of the formula I which is to be administered, and the frequency of administration depend on the strength of action and duration of action of the compound used; and, in addition, on the nature and severity of the disease which is to be treated, as well as on the sex, age, weight and individual response of the mammal which is to be treated. On average, the recommended daily dose of compound of the formula I for a patient weighting about 75 kg is at least 0.1 mg, preferably at least 1 mg, up to a maximum of 100 mg, preferably up to a maximum of 10 mg. In this connection, several, for example up to 4, single doses a day may be necessary for acute episodes of the disease, for example for attacks of asthma or for renal colic, whereas just one dose may suffice for prophylaxis.

It is possible according to the invention to obtain, for example, the compounds of the Formula I listed in the following table.

1,6-Dihydro-1-[2-(2-pyridinylcarbonylamino)ethyl]-6-oxo-3-pyridinecarboxylic acid methyl ester 1,6-Dihydro-1-[2-(2-pyridinylcarbonylamino)ethyl]-6-oxo-3-pyridinecarboxylic acid 1,6-Dihydro-1-[3-(2-pyridinylcarbonylamino)-propyl]-6-oxo-3-pyridinecarboxylic acid methyl ester 1,6-Dihydro-1-[3-(2-pyridinylcarbonylamino)-propyl]-6-oxo-3-pyridinecarboxylic acid 1,6-Dihydro-1-[2-(3-pyridinylcarbonylamino)ethyl]-6-oxo-3-pyridinecarboxylic acid methyl ester 1,6-Dihydro-1-[2-(3-pyridinylcarbonylamino)ethyl]-6-oxo-3-pyridinecarboxylic acid 1,6-Dihydro-1-[3-(3-pyridinylcarbonylamino)-propyl]-6-oxo-3-pyridinecarboxylic acid methyl ester 1,6-Dihydro-1-[3-(3-pyridinylcarbonylamino)-propyl]-6-oxo-3-pyridinecarboxylic acid 1,6-Dihydro-1-[2-(4-pyridinylcarbonylamino)ethyl]-6-oxo-3-pyridinecarboxylic acid methyl ester 1,6-Dihydro-1-[2-(4-pyridinylcarbonylamino)ethyl]-6-oxo-3-pyridinecarboxylic acid 1,6-Dihydro-1-[3-(4-pyridinylcarbonylamino)-propyl]-6-oxo-3-pyridinecarboxylicacid methyl ester 1,6-Dihydro-1-[2-(3-pyridinylcarbonylamino)ethyl]-6-oxo-3-pyridinecarboxylic acid ethyl ester 1,6-Dihydro-1-[2-(3-pyridinylcarbonylamino)ethyl]-6-oxo-3-pyridinecarboxylic acid-2-propyl ester 1,6-Dihydro-1-[2-(3-pyridinylcarbonylamino)ethyl]-6-oxo-3-pyridinecarboxylic acid phenylmethyl ester 1,6-Dihydro-1-[2-(3-pyridinylcarbonylamino)ethyl]-6-oxo-3-pyridinecarboxylic acid methyl amide 1,6-Dihydro-1-[2-(6-chloro-3-pyridinylcarbonylamino)ethyl]-6-oxo-3-pyridinecarboxylic acid methyl ester 1,6-Dihydro-1-[2-(6-methyl-3-pyridinylcarbonylamino)ethyl]-6-oxo-3pyridinecarboxylic acid methyl ester 1,6Dihydro-1-[2-(N-methyl-3-pyridinylcarbonylamino)ethyl]-6-oxo-3-pyridinecarboxylic acid methyl ester 1,2-Dihydro-1-[2-(3-pyridinylcarbonylamino)ethyl]-2-oxopyridine 1,6-Dihydro-6-oxo-1-[2-(2-pyrazinylcarbonylamino)ethyl]-3-pyridinecarboxylic acid methyl ester 1,6-Dihydro-6-oxo-1-[2-(3-quinolinylcarbonylamino)ethyl]-3-pyridinecarboxylic acid methyl ester 1-(2-Benzoylaminoethyl)-1,6-dihydro-6-oxo-3-pyridinecarboxylic acid methyl ester 1-[2-(5-Chloro-2-methoxybenyoylamino)ethyl]-1,6-dihydro-6-oxo-3-pyridinecarboxylic acid methyl ester 1,6-Dihydro-6-oxo-N-(3-pyridinylcarbonylamino)-3-pyridinecarboxylic acid methyl ester 1,6-Dihydro-6-oxo-N-(3-pyridinylcarbonylamino)-3-pyridinecarboxylic acid methyl ester 1,6-Dihydro-1-(N-methyl-3-pyridinylcarbonylaminomethyl)-6-oxo-3-pyridinecarboxylic acid methyl ester 1,2-Dihydro-1-[2-(3-pyridinylcarbonylamino)ethyl]-2-oxo-4-pyridinecarboxylic acid methyl ester 1,6-Dihydro-1-[3-(2-pyridinylcarbonylamino)-propyl]-6-oxo-2opyridinecarboxylic acid-2-propyl ester 1,6-Dihydro-1-[2-(4-pyridinylcarbonylamino)-1-methylethyl]-6-oxo-3-pyridinecarboxylic acid methyl ester 1,2-Dihydro-1-[3-(N-methyl-2-pyrazinylcarbonylamino)propyl]-2-oxo-4pyridinecarboxylic acid methyl ester 1,2-Dihydro-1-[2-(3-pyridinylcarbonylamino-2-methylethyl]-2-oxo pyridine 1,6-Dihydro-1-[N-ethyl-3-pyridinylcarbonylaminomethyl)-6-oxo-3-pyridinecarboxylic acid phenylmethyl amide

PHARMACOLOGICAL DATA

Methods

To study the membrane potential $E_m$ of smooth muscle cells, the conventional glass microelectrode technique was used.

Pieces of main pulmonary artery were obtained from guinea pigs supplied by Hoechst Tierhaltung. They were mounted on a teflon ring and fixed with a rubber o-ring. The tissue was superfused in an organ bath with physiological salt solution (mmol/l: 128.0 NaCl, 4.7 KCl, 2,5 $CaCl_2$, 1.2 $NaH_2PO_4$, 14.4 $NaHCO_3$, 1.2 $MgCl_2$, 10.0 glucose, 0.1 $Ca^{2+}$+EDTA) at a temperature of 37° C. Gassing (95% $O_2$, 5% $CO_2$) was carried out in the storage vessel, from which the solution was pumped within 30 sec into the organ bath. Complete exchange of solution in the bath could be reached within 3 min.

Glass microelectrodes filled with 3 mol/l KCl (self-filling type, o.d. 1 mm), 3 mol/l KCl-Agar bridge, and high impedance preamplifier (WPI KS-700) were employed in the measurement of the smooth muscle membrane potential changes. After impalement, approximately 3 rain was allowed for the electrical recording to stabilize. After this, the cells were exposed to test substances in a concentration of $1*10^{-5}$ mol/l until the maximum effect had been achieved. The test substances were prepared in ethanol and diluted with physiological salt solution. In the final solution, ethanol concentration was $\leq 0.2$ per cent which itself has no influence on the membrane potential.

After testing the test substance and rinsing the tissue it was almost possible to test also the standard potassium channel opener cromakalim ($5*10^{-7}$ tool/l) in the same cells.

Results

In the main pulmonary artery of guinea pigs, the resting membrane potential was $-57.4 \pm 5.9$ mV (mean$\pm$sd, n=7). The standard potassium channel opener cromakalim ($5*10^{-7}$ mol/l) caused in the same cells a hyperpolarisation of $17.3 \pm 2.9$ mV (n=6). Test compounds shifted the membrane potential to more negative values which means that they are able to open potassium channels. The following hyperpolarisation values were obtained:

| | |
|---|---|
| example 5: | $29 \pm 6$ mVolt at $10^{-6}$ mol/l (n = 3) |
| | $14 \pm 1$ mVolt at $10^{-7}$ mol/l (n = 3) |
| example 15: | $28 \pm 2$ mVolt at $10^{-6}$ mol/l (n = 3) |
| | $26 \pm 4$ mVolt at $10^{-7}$ mol/l (n = 4) |
| cromakalim: | $18 \pm 2$ mVolt at $10^{-6}$ mol/ln (n = 3) |
| | $14 \pm 1$ mVolt at $10^{-7}$ mol/l (n = 4) |

EXAMPLE

Example 1

1,6-Dihydro-1-[2-(2-pyridinylcarbonylamino)ethyl]-6-oxo-3-pyridinecarboxylic acid methyl ester To a 500 ml round bottomed flask fitted with a magnetic stirrer bar, addition funnel, and nitrogen inlet was added 1,2-diaminoethane (33.2 ml, 496 mmol) and absolute ethanol (80 ml). With stirring at room temperature, a solution consisting of 2-pyridinecarboxylic acid ethyl ester (25 g, 165.4 mmol) and absolute ethanol (80 ml) was added dropwise. Stirring was continued for 16 hours at which time the mixture was concentrated under reduced pressure. The resulting mixture was slurried in 2-propanol (400 ml) and filtered to remove the dimeric by-product 1,2-bis-(2-pyridinylcarbonylamino)ethane. The filtrate was concentrated and triturated with ether (2X). The ether solutions were combined and concentrated affording the desired 2-(2-aminoethyl)pyridinecarboxamide as an oil, which was used without further purification.

To a 250 ml round bottomed flask fitted with a magnetic stirrer bar and containing the above amine (1.79 g, 10.85 mmol) as an absolute ethanol (70 ml) solution was added 2-oxo-2H-pyran-5-carboxylic acid methyl ester (methylcoumalate, 1.67 g, 10.85 mmol) with stirring at room temperature. A slight precipitate formed immediately which was removed by filtration. The reaction mixture was diluted with absolute ethanol (20 ml) and stirring continued 16 hours, during which time a precipitate again formed. Partial concentration of the mother liquor led to precipitation of the desired product which was recrystallized from methanol, MP: 143°–145 ° C.

Example 2

1,6-Dihydro-1-[2-(2-pyridinylcarbonylamino)ethyl]-6-oxo-3-pyridinecarboxylic acid To a 10 ml round bottomed flask fitted with a magnetic stirrer bar was added 1,6-dihydro-1-[2-(2-pyridinylcarbonylamino)ethyl]-6-oxo-3-pyridinecarboxylic acid methyl ester (0.177 g, 0.59 mmol), methanol (1.4 ml), water (1.4 ml), and 15% aqueous sodium carbonate (1.4 ml). The resulting suspension was heated in a 60° C. oil bath for 1 hour during which time the mixture was completely solvated. Upon cooling to room temperature, acetic acid was added dropwise, with stirring, to a final pH of 5.5. The precipitated product was recovered by filtration, washed with water, and dried at 50° C. under high vacuum, MP: 266°–268° C.

Example 3

1,6-Dihydro-1-[3-(2-pyridinylcarbonylamino)propyl]-6-oxo-3-pyridinecarboxylic acid methyl ester (Using a procedure similar to Example 1,)

1,3-diaminopropane (41.4 ml, 496 mmol, in 80 ml abs. ethanol) was reacted with 2-pyridinecarboxylic acid ethyl ester (25.0 g, 165.4 mmol, in 80 ml absolute ethanol). After 6 hours, the reaction mixture containing 2-(3-aminopropyl)pyridinecarboxamide was concentrated and used without purification.

To a 500 ml round bottomed flask fitted with a magnetic stirrer bar and a nitrogen inlet was added the above amine (7.74 g, 43.2 mmol) and absolute ethanol (100 ml). With stirring at room temperature, a solution consisting of 2-oxo-2H-pyran-5-carboxylic acid methyl ester (6.33 g, 41.0 mmol) and absolute ethanol (100 ml). After 18 hours, the reaction mixture was concentrated. Purification via flash column chromatography (2 columns, silica gel, 2–5% methanol/dichloromethane) gave the desired product, MP: 115°–116° C.

Example 4

1,6-Dihydro-1-[3-(2-pyridinylcarbonylamino)propyl]-6-oxo-3-pyridinecarboxylic acid (Following a procedure similar to Example 2,)

1,6-dihydro-1-[3-(2-pyridinylcarbonylamino)propyl]-6-oxo-3-pyridinecarboxylic acid methyl ester (0.260 g, 0.83 retool) was hydrolysed in a mixture consisting of methanol (1.0 ml), water (1.0 ml), and 15% aqueous sodium carbonate (2.0 ml) at 60° for 1.5 hours. The solution was filtered and acidified (to pH 5.5 with acetic acid). The precipitated product was recovered by filtration, washed with water, and dried, MP: 180°–182° C.

Example 5

1,6-Dihydro-1-[2-(3-pyridinylcarbonylamino)ethyl]-6-oxo-3-pyridinecarboxylic acid methyl ester (Using a procedure similar to Example 1,)

1,2-diaminoethane (24.8 ml, 368 mmol, in 70 ml absolute ethanol) was reacted with 3-pyridinecarboxylic acid ethyl ester (50 g, 362 mmol in 70 ml absolute ethanol). After 18 hours, the resulting suspension was diluted with isopropanol (100 ml) and filtered. The flitrate was concentrated. Purification via flash column chromotography (silica gel, 17–33% methanol/dichloromethane) afforded 3-(2(aminoethyl)pyridinecarboxamide.

The above amine (0.70 g, 4.25 mmol) in absolute ethanol (15.0 ml) was reacted with 2-oxo-2Hopyran-5-carb dissolved in absolute ethanol (18.0 ml). The precipitated product was recovered by filtration, MP: 189°–190° C.

Example 6

1,6-Dihydro-1-[2-(3-pyridinylcarbonylamino)ethyl]-6-oxo-3-pyridinecarboxylic acid (Following a procedure similar to Example 2,)

1,6-dihydro-1-[2-(3-pyridinylcarbonylamino)ethyl]-6-oxo-3-pyridinecarboxylic acid methyl ester (0.39 g, 1.3 mmol) was hydrolysed in a mixture of methanol (3.9 ml), water (3.9 ml), and 15% aqueous sodium carbonate (3.9 ml) at 65°–70° C. for 1.5 hours. The solution was acidified (to pH 5.5 with acetic acid). The precipitated product was recovered by filtration, washed with water, and dried, MP: >295° C.

Example 7

1,6-Dihydro-1-[3-(3-pyridinylcarbonylamino)propyl]-6-oxo-3-pyridinecarboxylic acid methyl ester (Using a procedure similar to Example 1,)

1,3-diaminopropane (15.1 ml, 182 mmol, in abs. ethanol, 60 ml) was reacted with 3-pyridinecarboxylic acid methyl ester (24.8 g, 181.0 mmol) at room temperature to reflux for 7 hours. Upon cooling to room temperature, isopropanol was added (80 ml) and the mixture cooled to −5° C. The resulting precipitated by-product was removed by filtration. Concentration of the flitrate and purification via flash column chromatography (silica gel, 1% triethylamini/24% methanol/dichloromethane) gave 3-(3-aminopropyl)pyridinecarboxamide.

The above amine (1.79 g, 10.0 mmol), dissolved in abs. ethanol, 25 ml) was reacted with 2-oxo-2H-pyran-5-carboxylic acid methyl ester (1.54 g, 10.0 mmol, dissolved in absolute ethanol, 30 ml) for 16 hours at room temperature followed by 1.5 hours at reflux. The mixture was concentrated and the product purified by flash column chromatography (silica gel, 2–4% methanol/dichloromethane) affording the product, MP: 153°–156° C.

Example 8

1,6-Dihydro-1-[3-(3-pyridinylcarbonylamino)propyl]-6-oxo-3-pyridinecarboxylic acid (Following a procedure similar to Example 2,)

1,6-dihydro-1-[3-(3-pyridinylcarbonylamino)propyl]-6-oxo-3-pyridinecarboxylic acid methyl ester (0.18 g, 0.57 mmol) was hydrolysed in a mixture consisting of methanol (0.7 ml), water (0.7 ml), and 15% aqueous sodium carbonate (0.7 ml) at 60° C. for 1.3 hours. The solution was acidified (to pH 5.5 with acetic acid). The precipitated product was recovered by filtration, washed with water, and dried, MP: 218°–220° C.

Example 9

1,6-Dihydro-1-[2-(4-pyridinylcarbonylamino)ethyl]-6-oxo-3-pyridinecarboxylic acid methyl ester (Following a procedure similar to Example 1,)

1,2odiaminoethane (33.4 ml, 500 mmol, in abs. methanol, 40 ml) was reacted with 4-pyridinecarboxylic acid methyl ester (35.0 ml, 250 mmol, in absolute methanol, 40 ml). After 6 hours, the dimeric by-product, 1,2obis-(4-pyridinylcarbonylamino)ethane, was removed and the product 4-(2-aminoethyl)pyridinecarboxamide used without purification.

The above amine (1.65 g, 10.0 mmol, dissolved in abs. ethanol, 20 ml) was reacted with 2-oxo-2H-pyran-5-carboxylic acid methyl ester (1.54 g, 10.0 mmol, dissolved in absolute ethanol, 20 ml). After 18 hours, the precipitated product was recovered by filtration, washed with ether/ethanol (3:1 by volume), and dried, MP: 203°–204° C.

Example 10

1,6-Dihydro-1-[2-(4-pyridinylcarbonylamino)ethyl]-6-oxo-3-pyridinecarboxylic acid (Following a procedure similar to Example 2,)

1,6-dihydro-1-[2-(4-pyridinylcarbonylamino)ethyl]-6-oxo-3-pyridinecarboxylic acid methyl ester (0.600 g, 2.0 mmol) was hydrolysed in a mixture consisting of methanol (4.0 ml), water (0.7 ml), and 15% aqueous sodium carbonate (6.0 ml) at 75°–80° C. for 1.25 hours. The solution was acidified (to pH 5.5 with acetic acid). The precipitated product was recovered by filtration, washed with water, and dried, MP: >300° C.

Example 11

1,6-Dihydro-1-[3-(4-pyridinylcarbonylamino)propyl]-6-oxo-3-pyridinecarboxylic acid methyl ester (Following a procedure similar to Example 1,)

1,3-diaminopropane (52.0 ml, 625 mmol, in absolute ethanol, 60 ml) was reacted with 4-pyridinecarboxylic acid methyl ester (35.0 ml, 250 retool, in abs. ethanol, 60 ml). After 8 hours and stirring at room temperature to 80° C., the mixture was cooled to room temperature, filtered, and concentrated. Purification via flash column chromotography (silica gel, 14–20% water/acetone) gave the purified 4-(3-aminopropyl)pyridinecarboxamide.

The above amine (6.05 g, 33.8 mmol), slurried in absolute ethanol (130 ml) was reacted with 2-oxo-2H-pyran-5-carboxylic acid methyl ester (5.20 g, 33.8 mmol). After 18 hours, a precipitated by-product was removed by filtration, .washed with ethanol, and the flitrate concentrated. The crude product was purified via flash column chromatography (silica gel, 5% methanol/dichloromethane) and medium pressure liquid chromatography (silica gel, 5% methanol/ethyl acetate). Trituration with ether gave a white solid product, MP: 133°–135° C.

Example 12

1,6-Dihydro-1-[2-(3-pyridinylcarbonylamino)ethyl]-6-oxo-3-pyridinecarboxylic acid ethyl ester To a 10 ml round bottomed flask fitted with a magnetic stirrer bar, reflux condensor, and nitrogen inlet was added 1,6-dihydro-1-[2-(3-pyridinylcarbonylamino)ethyl]-6-oxo-3-pyridinecarboxylicacid (0.14 g, 0.49 mmol) and thionyl chloride (3.0 ml). The mixture was heated for 1 hour at reflux, cooled to room temperature, and concentrated. The residue was suspended in absolute ethanol (7.0 ml) and 4-dimethylaminopyridine (1 mg). Pyridine (0.12 ml, 1.47 mmol) was added with stirring at room temperature. After 16 hours, the mixture was concentrated. Purification via medium liquid chromotography (silica gel, 5–10% methanol/dichloromethane) gave the desired ester, MP: 240°–242° C.

Example 13

1,6-Dihydro-1-[2-(3-pyridinylcarbonylamino)ethyl]-6-oxo-3-pyridinecarboxylic acid-2-propyl ester To a 25 ml round bottomed flask fitted with a magnetic stirrer bar, reflux condensor, and nitrogen inlet was added 1,6-dihydro-1-[2-(3-pyridinylcarbonylamino)ethyl]-6-oxo-3-pyridinecarboxylicacid (0.20 g, 0.70 mmol) and thionyl chloride (5.0 ml). The mixture was heated at reflux for 2 hours, cooled to room temperature, and concentrated. The residue was suspended in 2-propanol (5.0 ml) and 4-dimethylaminopyridine (1 mg). Pyridine (0.17 ml, 2.1 mmol) was added with stirring at room temperature. After 16 hours, the reaction mixture was concentrated. Purification via flash column chromatography (silica gel, 5% methanol/dichloromethane) and repurification via medium pressure liquid chromatography (silica gel, 5% methanol/dichloromethane) gave the desired product, MP: 160°–161 ° C.

Example 14

1,6-Dihydro-1-[2-(3-pyridinylcarbonylamino)ethyl]-6-oxo-3-pyridinecarboxylic acid phenylmethyl ester To a 10 ml round bottomed flask fitted with a magnetic stirrer bar and nitrogen inlet was added 1,6-dihydro-1-[2-(3-pyridinylcarbonylamino)ethyl]-6-oxo-3-pyridinecarboxylic acid (0.20 g, 0.70 mmol), dimethylformamide (5.0 ml), potassium hydrogen carbonate (0.175 g, 1.75 mmol), and benzyl bromide (0.082 ml, 0.69 mmol). The resulting suspension was heated in a 50° C. oil bath with stirring. After 2 hours, the solution was concentrated and the residue suspended in dichloromethane-methanol and water. The layers were separated and the organic layer washed with water and the combined aqueous layers back-extracted with dichloromethane (2X). The combined organic layers were dried (Na₂SO₄). Filtration, concentration, and purification via medium pressure liquid chromatography (silica gel, 5% methanol/dichloromethane) afforded the desired product as a white powder, MP: 154°–155° C.

Example 15

1,6-Dihydro-1-[2-(3-pyridinylcarbonylamino)ethyl]-6-oxo-3-pyridinecarboxylic acid methyl amide To a 100 ml round bottomed flask fitted with a magnetic stirrer bar and nitrogen inlet was added 1,6-dihydro-1-[2-(3-pyridinylcarbonylamino)ethyl]-6-oxo-3-pyridinecarboxylic acid (0.22 g, 0.77 mmol) methylamine hydrochloride (0.104 g, 1.54 mmol), and dimethylformamide (25.5 ml). The reaction mixture was cooled in a −8° C. ice bath and treated with triethylamine (1.07 ml, 7.7 mmol) and propylphosphonic acid anhydride (0.55 ml, added as a 0.55 ml ethyl acetate solution, Angew. Chemie 1980, 92(2), 129). The flask was allowed to warm slowly to room temperature and stirred for 2.25 hours. The mixture was concentrated, slurried in aqueous sodium bicarbonate, and again concentrated. The residue was slurried in methanol and filtered. Further purification of the solid recovered from filtration via flash column chromotography (silica gel, 15–20% methanol/dichloromethane) gave the product, MP: 208°–210° C.

Example 16

1,6-Dihydro-1-[2-(6-chloro-3-pyridinylcarbonylamino)ethyl]-6-oxo-3-pyridinecarboxylic acid methyl ester To a 500 ml 3-necked flask fitted with a magnetic stirrer bar, addition funnel, nitrogen inlet, and containing 2-oxo-2H-pyran-5-carboxylic acid methyl ester (coumalic acid methyl ester) (10.0 g, 65.0 mmol) and absolute ethanol 160 ml) was added, over 3-5 minutes at room temperature, a solution consisting of 1,2-diaminoethane (17.4 ml, 260 mmol) and abs. ethanol (50 ml). Stirring was continued for 4 hours at which time the suspension was filtered. Concentration of the flitrate gave 1-(2-aminoethyl)-1,6-dihydro-6-oxo-3-pyridinecarboxylic acid methyl ester which was used without purification.

To a 1 00 ml round bottomed flask fitted with a magnetic stirrer bar and nitrogen inlet was added the above amine (0.300 g, 1.53 mmol), 6-chloro-3-pyridinecarboxylic acid (0.241 g, 1.53 mmol), and dry dichloromethane 125.5 mmol). Upon cooling in a −8° C. ice bath with stirring, triethyl amine (1.07 ml, 7.65 mmol) and propylphosphonic acid anhydride (0.50 ml, added as a 0.50 ml ethyl acetate solution, Angew. Chemie 1980, 92(2), 129) were added. The flask was allowed to warm slowly to room temperature over 1.25 hours. Stirring was continued 30 minutes at which time the reaction mixture solution was washed with aqueous sodium bicarbonate (2X), brine, and dried (Na₂SO₄). Filtration, concentration and purification via medium pressure liquid chromatography (silica gel, 4% methanol/dichloromethane) have the desired product, MP: 188°–190° C.

Example 17

1,6-Dihydro-1-[2-(6-methyl-3-pyridinylcarbonylamino)ethyl]-6-oxo-3-pyridinecarboxylic acid methyl ester (Similar to Example 16), 1-(2-aminoethyl)-1,6-dihydro-6-oxo-3-pyridinecarboxylic acid methyl ester (0.50 g, 2.55 mmol) was coupled with 6-methyl-3-pyridinecarboxylic acid (0.42 g, 3.1 mmol)in dimethylformamide (42.5 ml) with triethylamine (1.80 ml, 12.75 mmol) and propylphosphonic acid anhydride (0.90 ml, added as a 0.90 ml ethyl acetate solution). After 72 hours, dichloromethane and aqueous sodium bicarbonate were added. The layers were separated and the organic layer washed with brine and dried (Na₂SO₄). Filtration, concentration, and purification by medium pressure liquid chromatography (silica gel, 4–6% methanol/dichloromethane) gave the desired product, MP: 184°–185° C.

Example 18

1,6-Dihydro-1-[2-(N-methyl-3-pyridinylcarbonylamino)ethyl]-6-oxo-3-pyridinecarboxylic acid methyl ester To a round bottomed 25 ml flask fitted with a magnetic stirrer bar and nitrogen inlet was added 1,6-dihydro-1-[2-(3-pyridinylcarbonylamino)ethyl]-6-oxo-3-pyridinecarboxylic acid methyl ester (0.211 g, 0.70 mmol) and dimethylformamide (7.0 ml). At room temperature with stirring, sodium hydride (0.018 g, 0.77 mmol, 98% dry) was added. After 45 minutes, the reaction was quenched with dimethylsulfate (0.073 ml, 0.78 mmol). Stirring was continued for 3.75 hours at which time the mixture was concentrated. The crude product was purified by medium pressure liquid chromotography (silica gel, 3% methanol/dichloromethane) and triturated with ether to give the product, MP: 120°–122° C.

Example 19

1,2-Dihydro-1-[2-(3-pyridinylcarbonylamino)ethyl]-2-oxopyridine

To a 1|2-necked flask fitted with a magnetic stirrer bar and a nitrogen inlet was added 2-hydroxypyridine (10.0 g, 105.0 mmol) and dimethylformamide (300 ml). The resulting suspension was cooled in a 0° C. ice bath and sodium hydride (2.70 g. 110 mmol, 98% dry) was added. The flask was allowed to warm to room temperature over 25 minutes after which time a solution consisting of N-(2-bromoethyl)phthalimide (29.3 g, 115.5 mmol) and dimethylformamide (50 ml) was added, followed by potassium iodide (0.35 g). The reaction mixture was heated in a 50° C. oil bath for 4.5 hours, cooled to room temperature, and concentrated. The residue was slurried in dichloromethane, filtered, and the flitrate concentrated. Trituration of the resulting solid with ether (2X) followed by drying gave 1,2-dihydro-1-(2-N-phthalimidoethyl)-2-oxopyridine, MP: 187°–189° C.

To a 250 ml round bottomed flask fitted with a magnetic stirrer bar, reflux condensor, and nitrogen inlet was added the above phthalimide (2.00 g, 7.5 mmol), absolute ethanol (75 ml), and anhydrous hydrazine (0.71 ml, 22.5 mmol). The mixture was heated at reflux for 45 minutes, cooled to room temperature, and the by-product phthalimide precipitate removed by filtration. The flitrate was concentrated and residual hydrazine removed by azeotroping with toluene and high vacuum. The intermediate 1-(2-aminoethyl)-1,2-dihydro-2-oxopyridine was used immediately below without purification.

The above amine (7.5 mmol) was dissolved in dimethylformamide (40 ml), and 4-dimethylaminopyridine (1 mg), and diisopropylethylamine (3.90 ml, 22.5 mmol) added. With stirring, the solution was cooled to 0° C. and 3-pyridinecarboxylic acid chloride hydrochloride (1.47 g, 8.25 mol) was added. The flask was allowed to warm to room temperature and stirring continued 3.5 hours. The mixture was concentrated and the crude product purified by flask column chromatography (silica gel, 5% methanol/dichloromethane). The product was redissolved in dichloromethane and aqueous potassium carbonate. The layers were separated and the aqueous layer extracted with dichloromethane (2X) and ether (1X). The combined organic layers were dried ($K_2CO_3$), filtered, and concentrated to give the desired product, MP: 158°–159° C.

Example 20

1,6-Dihydro-6-oxo-1-[2-(2-pyrazinylcarbonylamino)ethyl]-3-pyridinecarboxylic acid methyl ester (Similar to Example 16,)

1-(2-aminoethyl)-1,6-dihydro-6-oxo-3-pyridinecarboxylic acid methyl ester (0.396 g, 2.02 mmol) was coupled with 2-pyrazinecarboxylic acid (0.251 g, 2.02 mmol) in a mixture of dichloromethane (34 ml) and dimethylformamide (35 ml) with triethylamine (1.41 ml, 10.1 mmol)and propylphosphonic acid anhydride (0.7 ml, added as a 0.7 ml ethyl acetate solution). After 18 hours, the mixture was concentrated and the residue slurried in dichloromethane and aqueous sodium bicarbonate. The layers were separated and the aqueous layer extracted with dichloromethane (2X) and the combined organic layers dried ($Na_2SO_4$). Filtration, concentration, and purification via medium pressure liquid chromatography (silica gel, 5% methanol/dichloromethane) gave the desired product, MP: 195°–197° C.

Example 21

1,6-Dihydro-6-oxo-1-[2-(3-quinolinylcarbonylamino)ethyl]-3-pyridinecarboxylic acid methyl ester (Similar to Example 16,)

1-(2-aminoethyl)-1,6-dihydro-6-oxo-3-pyridinecarboxylic acid methyl ester (0.400 g, 2.0 mmol) was coupled with 3-quinolinecarboxylic acid (0.373 g, 2.2 mmol) in dichloromethane (35 ml) with triethylamine (1.40 ml, 10.0 mmol) and propylphosphoric acid anhydride (0.65 ml, added as a 0.65 ml ethyl acetate solution). After 17 hours, the solution was filtered through a pad of celite and the filtrate concentrated. Dichloromethane and aqueous sodium bicarbonate were added the layers separated. The aqueous layer was extracted with dichloromethane (2X) and the combined organic layers washed with aqueous sodium bicarbonate, brine, dried ($Na_2SO_4$), filtered, and concentrated. Recrystallisation from 1,2-dichloroethane gave the pure product, MP: 174°–175° C.

Example 22

1-(2-Benzoylaminoethyl)-1,6-dihydro-6-oxo-3-pyridinecarboxylic acid methyl ester To a 500 ml round bottomed flask fitted with a magnetic stirrer bar and nitrogen inlet was added 1-(2-aminoethyl)-1-6-dihydro-6-oxo-3-pyridinecarboxylic acid methyl ester (1.65 g, 8.4 mmol), dichloromethane (200 ml), pyridine (3.90 ml, 48.6 mmol), and 4-dimethylaminopyridine (5 mg). Upon cooling to 0° C. with stirring, benzoyl chloride (3.80 ml, 32.4 mmol) was added and the flask allowed to warm to room temperature. Stirring was continued at room temperature for 16 hours, at which time the reaction mixture was extracted with aqueous 1N HCl (2X). The combined aqueous layers were back-extracted with dichloromethane and the combined organic layers washed with brine and dried ($MgSO_4$), filtered, and concentrated. The crude product was slurried in dichloromethane and the insoluble portion removed by filtration. Concentration and recrystallisation from methanol gave the desired product in pure form, MP: 190°–191 ° C.

Example 23

1-[2-(5-Chloro-2-methoxybenzoylamino)ethyl]-1,6-dihydro-6-oxo-3-pyridinecarboxylic acid methyl ester (Similar to Example 22,)

1-(2-aminoethyl)-1,6-dihydro-6-oxo-3-pyridinecarboxylic acid methyl ester (0.985 g, 5.0 mmol) was reacted with 5-chloro-2-methoxybenzoyl chloride (1.04 g, 5.1 mmol) in dichloromethane (25 ml) and pyridine (10 ml). After an aqueous work-up, purification via flash column chromatography (silica gel, 8% methanol/dichloromethane) gave the product, MP: 149°–150° C.

Example 24

1,6-Dihydro-6-oxo-N-(3-pyridinylcarbonylamino)-3-pyridinecarboxylic acid methyl ester (Similar to Example 16,)

2-oxo-2H-pyran-5-carboxylic acid methyl ester (7.50 g, 48.7 mmol, dissolved in methanol, 50 ml) was reacted with anhydrous hydrazine (3.90 ml, 80.2 mmol, dissolved in methanol, 20 ml) at 0° C. for 70 minutes followed by 2 hours at room temperature. The mixture was filtered to remove a precipitate present. The flitrate was concentrated, the residue slurried in absolute ethanol and heated at reflux for 40 minutes. The suspension was filtered and the flitrate concentrated to give an oil. Dichloromethane and water were added and the layers separated. The aqueous layer was extracted with dichloromethane (2X), and the combined organic layers were dried ($K_2CO_3$), filtered, and concentrated, affording the pure N-amino-1,6-dihydro-6-oxo-3-pyridinecarboxylic acid methyl ester, MP: 136°–137° C.

Similar to Example 22, the above amine (0.470 g, 2.8 retool, dissolved in dichloromethane, 30 ml) was reacted with 3-pyridinecarboxylic acid chloride hydrochloride (0.516 g, 3.1 mmol) with pyridine (0.50 ml, 6.2 mmol) at 0° C. to room temperature for 16 hours. Additional acid chloride (0.228 g. 1.2 retool) and pyridine (0.21 ml, 2.6 mmol) were added and stirring continued 1.5 hours. The solution was extracted with aqueous sodium bicarbonate (2X), water (2X), and dried ($Na_2SO_4$). Filtration, concentration, and trituration with t-butylmethylether at reflux followed by cooling to room temperature gave the product, MP: 172°–173° C.

Example 25

1,6-Dihydro-6-oxo-N-(3-pyridinylcarbonylamino)-3-pyridinecarboxylic acid (Similar to Example 2,)

1,6-dihydro-6-oxo-N-(3-pyridinylcarbonylamino)-3-pyridinecarboxylicacid methyl ester (0.085 g, 0.31 mmol) was hydrolysed in a mixture consisting of water (0.4 ml), methanol (0.4 ml), and 15% aqueous sodium carbonate (0.4 ml) at 68° C. for 6.5 hours. The solution was acidified (to pH 5.5 with acetic acid). The precipitated product was recovered by filtration, washed with water, and dried, MP: >250° C.

We claim:

1. An arylcarbonylaminoalkyl-dihydro-oxo-pyridine of Formula I:

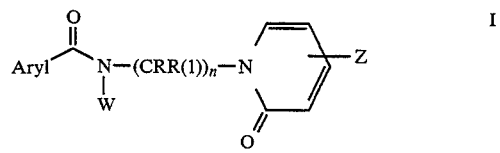

wherein aryl is a pyridinyl system unsubstituted or substituted with 1 or 2 identical or different halogen, loweralkyl, alkoxy, or trifluoromethyl radicals;

n is zero, 2 or 3;

R and R(1), independently for each carbon are hydrogen, or loweralkyl;

W is hydrogen or loweralkyl;

Z is hydrogen, (CO)OR(2) or (CO)NR(2)$_2$;

R(2) is independently hydrogen or loweralkyl;

and the geometrical isomers or optical antipodes thereof.

2. The compound of claim 11 comprising 1,6-dihydro-1-[2-(2-pyridinylcarbonylamino)ethyl]-6-oxo-3-pyridinecarboxylic acid methyl ester.

3. A method of treating hypertension, angina pectoris, cardiac insufficiency, disturbances of peripheral blood flow, disturbances of intestinal motility, premature labor, obstructions of the airways, urinary tract or biliary tract, or spastic states comprising administering to a mammal in need of treatment an effective amount of a pyridine according to claim 1.

4. A pharmaceutical compound for the treatment of hypertension, angina pectoris, cardiac insufficiency, disturbances of peripheral blood flow, disturbances of intestinal motility, premature labor, obstructions of the airways, urinary tract or biliary tract, or spastic states comprising an effective amount for said treatment of a pyridine according to claim 1 and a pharmaceutically acceptable carrier or diluent.

* * * * *

UNITED STATES PATENT AND TRADEMARK OFFICE
CERTIFICATE OF CORRECTION

PATENT NO. : 5,360,808
DATED : November 01, 1994
INVENTOR(S) : Heinrich ENGLERT et al It is certified that error appears in the above-indentified patent and that said Letters Patent is hereby corrected as shown below:

Abstract, Title Page, Line 27, change "1" to --I--.

Claim 2, Column 18, Line 26, change "11" to --1--.

Claim 4, Column 18, Line 36, change "compound" to --composition--

Signed and Sealed this

Thirtieth Day of May, 1995

Attest:

BRUCE LEHMAN

*Attesting Officer*   *Commissioner of Patents and Trademarks*